United States Patent
Chou

(10) Patent No.: US 12,059,448 B2
(45) Date of Patent: *Aug. 13, 2024

(54) PHARMACEUTICAL COMPOSITION COMPRISING THROMBOLYTIC PEPTIDE-TETRAHYDROISOQUINOLINE CONJUGATE

(71) Applicant: Lumosa Therapeutics Co., LTD, Taipei (TW)

(72) Inventor: David Chih-Kuang Chou, Taipei (TW)

(73) Assignee: LUMOSA THERAPEUTICS CO., LTD (TW)

( * ) Notice: Subject to any disclaimer, the term of this patent is extended or adjusted under 35 U.S.C. 154(b) by 0 days.

This patent is subject to a terminal disclaimer.

(21) Appl. No.: 18/333,388

(22) Filed: Jun. 12, 2023

(65) Prior Publication Data
US 2024/0024407 A1   Jan. 25, 2024

Related U.S. Application Data

(63) Continuation of application No. 17/664,539, filed on May 23, 2022, now Pat. No. 11,707,501, which is a continuation of application No. 17/031,368, filed on Sep. 24, 2020, now Pat. No. 11,338,008.

(60) Provisional application No. 62/905,679, filed on Sep. 25, 2019.

(51) Int. Cl.
*A61K 38/06* (2006.01)
*A61K 47/26* (2006.01)
*A61K 47/54* (2017.01)
*A61K 47/62* (2017.01)

(52) U.S. Cl.
CPC .............. *A61K 38/06* (2013.01); *A61K 47/26* (2013.01); *A61K 47/545* (2017.08); *A61K 47/62* (2017.08)

(58) Field of Classification Search
CPC ........ A61K 38/06; A61K 47/26; A61K 47/62; A61K 47/545; A61K 38/07; A61K 47/55; A61K 9/19; A61K 9/0019
See application file for complete search history.

(56) References Cited

U.S. PATENT DOCUMENTS 11,338,008 B2 *  5/2022  Chou .................... A61K 47/62
11,707,501 B2 *  7/2023  Chou ................... A61K 9/0019
                                                       514/14.9

OTHER PUBLICATIONS

I.M. Pertseva et al. Auxiliary Substances and Their Use in Pharmacy in Pharmaceutical and Medical-Biological Aspects of Drugs, Eds I.M. Pertseva and I. A. Zupantsa., vol. 1, pp. 253-255, 1999.
Jorgensen et al., Recent trends in stabilising peptides and proteins in pharmaceutical formulation—considerations in the choice of excipients, Expert Opinion Drug Delivery, 2009, pp. 1219-1230, Informa UK Ltd, United Kingdom.
Wang et al., "Antibody Structure, Instability, and Formulation", Journal of Pharmaceutical Sciences, Jan. 2007, pp. 1-26, vol. 96, Wiley-Liss, Inc. and the American Pharmacists Association, DOI 10.1002/jps.
Yeh et al., "Study of a novel small molecule, LT3001, in a thromboembolic stroke model in non-human primates", Lumosa Therapeutics Co., Ltd., Taiwan, Apr. 2017.

* cited by examiner

*Primary Examiner* — Sudhakar Katakam
(74) *Attorney, Agent, or Firm* — Perkins Coie LLP; Viola T. Kung

(57) ABSTRACT

The present invention provides a pharmaceutical composition comprising a binary conjugate, DC009, which is a conjugate of a thrombolytic peptide (Pro-Ala-Lys) and a tetrahydroisoquinoline compound having two C1-4 alkyl groups via a lysine linking arm, and a pharmaceutical acceptable carrier. The composition has a pH less than 6.5, preferably has a pH about pH 2-5.5 The composition may comprise a pharmaceutical acceptable excipient such as mannitol, sorbitol, sucrose, lactose, or trehalose.

15 Claims, 1 Drawing Sheet

PHARMACEUTICAL COMPOSITION COMPRISING THROMBOLYTIC PEPTIDE-TETRAHYDROISOQUINOLINE CONJUGATE

This application is a continuation of U.S. application Ser. No. 17/664,539, filed May 23, 2022; which is a continuation of U.S. application Ser. No. 17/031,368, filed Sep. 24, 2020, now U.S. Pat. No. 11,338,008, issued May 24, 2022; which claims priority to U.S. Provisional Application No. 62/905,679, filed Sep. 25, 2019. The above identified applications are incorporated herein by reference in their entireties.

FIELD OF THE INVENTION

The present invention relates to a pharmaceutical composition comprising a thrombolytic peptide-tetrahydroisoquinoline conjugate and a pharmaceutically acceptable carrier having a pH less than pH 6.5.

DETAILED DESCRIPTION OF THE INVENTION

Figure 1A:
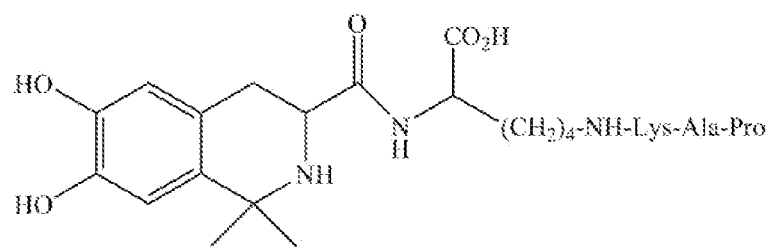
FIG. 1A shows the chemical structure of DC009.
Figure 1B:
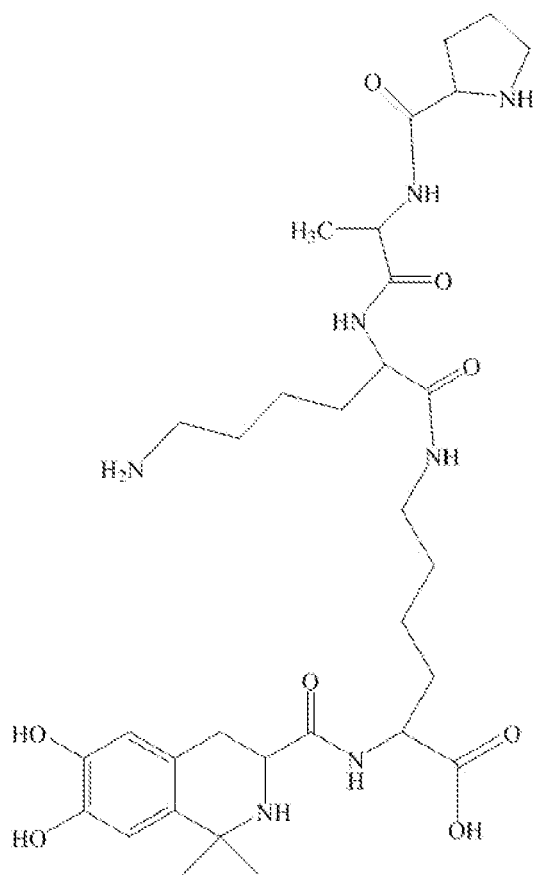
FIG. 1B shows the chemical structure of DC009 with the detail of NH-Lys-Ala-Pro.

Disclosed herein is a pharmaceutical composition comprising DC009, or a pharmaceutically acceptable salt thereof, and a pharmaceutically acceptable carrier. DC009 is also abbreviated as LT3001, with a chemical name of 3S-6,7-dihydroxy-1,1-dimethyl-1,2,3,4-tetrahydro-isoquinoline-3-acyl-Lys(Pro-Ala-Lys) or L-Lysine, N6-(L-prolyl-L-alanyl-L-lysyl)-N2-[[(3S)-1,2,3,4-tetrahydro-6,7-dihydroxy-1,1-dimethyl-3-isoquinolinyl]carbonyl] (CAS RN: 1639303-73-3). The structure of DC009 is shown in FIG. 1A, the amide bond between the Lysine linking arm and the Pro-Ala-Lys peptide is shown in FIG. 1B. DC009 is a binary conjugate that can be formed by coupling a thrombolytic peptide (Pro-Ala-Lys) and a tetrahydroisoquinoline compound having two C1-4 alkyl groups via a Lysine linking arm. The preparation of DC009 compound is disclosed in Example 63 of US Publication No. 2016-0083423, which is incorporated herein by reference. A pharmaceutical acceptable salt of DC009 includes any salt that are pharmaceutically acceptable; for example, a hydrochloride salt, i.e. L-lysine, N6-(L-prolyl-L-alanyl-L-lysyl)-N2-[[(3 S)-1,2,3,4-tetrahydro-6,7-dihydroxy-1,1-dimethyl-3-isoquinolinyl]carbonyl]-hydrochloride (1:3) (CAS RN: 2419930-71-3).

The term "pharmaceutically acceptable" means biologically or pharmacologically compatible for in vivo use in animals or humans. In some embodiments, "pharmaceutically acceptable" means approved by a regulatory agency of the Federal or a state government or listed in the U.S. Pharmacopeia or other generally recognized pharmacopeia for use in animals, and more particularly in humans.

In general, pharmaceutical compositions are prepared by uniformly and intimately bringing the active ingredient into association with a liquid carrier or a finely divided solid carrier or both, and then, if necessary, shaping the product into the desired formulation. In the pharmaceutical composition, the active object compound is included in an amount sufficient to produce the desired effect upon the process or condition of diseases. Accordingly, in some embodiments, the pharmaceutical compositions of the present invention encompass any composition made by admixing 0.1 to 50%, of the active ingredient with a pharmaceutically acceptable carrier. In yet other embodiments, the pharmaceutical compositions of the present invention encompass any composition made by admixing 0.1%, 0.2%, 0.3%, 0.4%, 0.5%, 0.6%, 0.7%, 0.8%, 0.9%, 1%, 1.5%, 2%, 2.5%, 3%, 3.5%, 4%, 5%, 6%, 7%, 8%, 9%, 10%, 15%, 20%, 25%, 30%, 35%, 40%, 45% or 50% of the active ingredient with a pharmaceutically acceptable carrier. In certain embodiments, the pharmaceutical compositions of the present invention encompass any composition made by admixing 0.2%-5%, of the active ingredient with a pharmaceutically acceptable carrier. In other embodiments, the pharmaceutical compositions of the present invention encompass any composition made by admixing 0.5% to 5%, of the active ingredient with a pharmaceutically acceptable carrier.

Pharmaceutically acceptable carriers, which are inactive ingredients, can be selected by those skilled in the art using conventional criteria. Pharmaceutically acceptable carriers include, but are not limited to, non-aqueous based solutions, suspensions, emulsions, microemulsions, micellar solutions, gels, and ointments. The pharmaceutically acceptable carriers may also contain ingredients that include, but are not limited to, saline and aqueous electrolyte solutions; ionic and nonionic osmotic agents such as sodium chloride, potassium chloride, glycerol, and dextrose; pH adjusters and buffers such as salts of hydroxide, phosphate, citrate, acetate, borate; and trolamine; antioxidants such as salts, acids and/or bases of bisulfite, sulfite, metabisulfite, thiosulfite, ascorbic acid, acetyl cysteine, cystein, glutathione, butylated hydroxyanisole, butylated hydroxytoluene, tocopherols, and ascorbyl palmitate; surfactants such as lecithin, phospholipids, including but not limited to phosphatidylcholine, phosphatidylethanolamine and phosphatidyl inositiol; poloxamers and ploxamines, polysorbates such as polysorbate 80, polysorbate 60, and polysorbate 20, polyvinyls such as polyvinyl alcohol and povidone; cellulose derivatives such as methylcellulose, hydroxypropyl cellulose, hydroxyethyl cellulose, carboxymethyl cellulose and hydroxypropyl methylcellulose and their salts; petroleum derivatives such as mineral oil and white petrolatum; fats such as lanolin, peanut oil, palm oil, soybean oil; mono-, di-, and triglycerides; polymers of acrylic acid such as carboxypolymethylene gel, and hydrophobically modified cross-linked acrylate copolymer; polysaccharides and glycosaminoglycans such as sodium hyaluronate. Such pharmaceutically acceptable carriers may be preserved against bacterial contamination using well-known preservatives, these include, but are not limited to, benzalkonium chloride, ethylene diamine tetra-acetic acid and its salts, benzethonium chloride, chlorhexidine, chlorobutanol, methylparaben, thimerosal, and phenylethyl alcohol, or may be formulated as a non-preserved formulation for either single or multiple use.

In some embodiment, the pharmaceutical composition comprises DC009 and a pharmaceutically acceptable carrier, wherein the composition has a pH<7 or a pH<6.5. In some embodiment, the composition has a pH about pH 1-pH 6. In some embodiment, the composition has a pH about pH 2-pH 5.5. In some embodiment, the composition has a pH about pH 3-pH 6. In some embodiment, the composition has a pH about pH 3.5-pH 5.5. In some embodiment, the composition has a pH about pH 3.5, pH 4, pH 4.5, pH 5 or pH 5.5. In some embodiments, the composition has a pH about 4.5.

As used in this application, "about" refers to ±5% of the recited value.

In some embodiments, the pharmaceutical composition comprises DC009 and a pharmaceutically acceptable excipient, wherein the pharmaceutically acceptable excipient is a disaccharide or a sugar alcohol.

In some embodiments, the sugar alcohol is mannitol, sorbitol, ethylene glycol, glycerol, erythritol, threitol, arabitol, xylitol, ribitol, galactitol, fucitol, Iditol, inositol, volemitol, isomalt, maltitol or lactitol. In some embodiments, the sugar alcohol is arabitol, xylitol, ribitol, mannitol, sorbitol, galactitol, fucitol, iditol, or inositol. In some embodiments, the sugar alcohol is arabitol, xylitol, ribitol, mannitol, sorbitol, galactitol, fucitol, Iditol or inositol. A preferred sugar alcohol is mannitol or sorbitol.

In some embodiments, the disaccharide is sucrose, lactose, trehalose (β,β-trehalose, α,β-trehalose), lactulose, maltose, cellobiose, chitobiose, kojibiose, nigerose, sophorose, laminaribiose, gentiobiose, turanose, maltulose, palatinose, gentiobiulose, mannobiose, melibiose, melibiulose, rutinose, rutinulose or xylobiose. In some embodiments, the disaccharide is sucrose, lactulose, lactose, trehalose, cellobiose or chitobiose. A preferred disaccharide is sucrose, lactose, or trehalose.

In the present application, the weight ratio of DC009 versus the pharmaceutically acceptable excipient (DC009/excipient ratio) may be expressed as either, for example, 9:1 or 9. For example, a DC009/excipient ratio expressed as 0.5:1 is the same as a DC009/excipient ratio expressed as 0.5. A range of DC009/excipient ratios may be expressed as 1:1-9:1 for example.

In some embodiments, the pharmaceutical composition comprises DC009 and a pharmaceutically acceptable excipient, wherein the pharmaceutically acceptable excipient is mannitol, sorbitol, sucrose, lactose or trehalose, and wherein the weight ratio of DC009 versus the pharmaceutically acceptable excipient is 1:1-1:9. If the ratio is lower than 1:1, the volume is too small to be lyophilized, and if the ratio is higher than 1:9, the osmolarity is too high for intravenous use.

In some embodiments, the ratio of DC009 versus the pharmaceutically acceptable excipient is 1:9. In one embodiment, the pharmaceutical composition comprises about 1% DC009, and about 9% pharmaceutically acceptable excipient. For example, the pharmaceutically acceptable excipient is sucrose, lactose, sorbitol or trehalose.

In some embodiments, the pharmaceutical composition comprises DC009 and a pharmaceutically acceptable excipient, wherein the pharmaceutically acceptable excipient is mannitol, and the weight ratio of DC009 versus mannitol is 1:1-1:7, preferably 1:1-1:5. For example, the weight ratio of DC009 versus mannitol is about 1:1, 1:1.3, 1:3.8, or 1:5. In various embodiments, the weight ratio of DC009 versus mannitol is 1:5. In one embodiment, the pharmaceutical composition comprises about 1% DC009, and about 5% mannitol.

In various embodiments, the ratio of DC009 versus the pharmaceutically acceptable excipient is about 1:3.8. In one embodiment, the pharmaceutical composition comprising about 1% DC009, and about 3.8% mannitol. In one embodiment, the pharmaceutical composition comprising about 4% DC009, and about 14.8% mannitol.

In various embodiments, the ratio of DC009 versus the pharmaceutically acceptable excipient is about 1:1.3. In some embodiments, the pharmaceutical composition comprises about 2% DC009, and about 2.6% mannitol.

In some embodiments, the pharmaceutical composition comprises about 1% DC009, and about 3.8% mannitol, and wherein the composition has a pH of about pH 3.5-pH 5.5, more preferably, the composition has a pH of about pH 4.5.

In some embodiments, the pharmaceutical composition comprises about 2% DC009, and about 2.6% mannitol, and wherein the composition has a pH of about pH 3.5-pH 5.5, more preferably, the composition has a pH about 4.5.

The following examples further illustrate the present invention. These examples are intended merely to be illustrative of the present invention and are not to be construed as being limiting.

EXAMPLES

Example 1. Preparation and Purity Determination for DC009

DC009 were prepared according to the US Publication Application No. 2016-0083423. The final product was washed repetitively by DCM, THF and ethyl ether several times to increase the purity of the final product. The concentration and purity of DC009 in a solution are determined by HPLC with the following conditions.

Column: alkyl reversed-phase bounded phase column

Mobile Phase (MP): MP A: 0.1% by volume TFA in DI water/MP B: 0.1% by volume TFA in acetonitrile Detection Wavelength: 214 & 280 nm Column Temperature: 20-25° C.

Sample Temperature: 10-15° C.

Injection Volume: 10-20 μL

Gradient: MP A and MP B

In Examples 2-6, the stability of each formulation is shown as "assay recovery" or "relative purity level". Samples at each time point was analyzed by HPLC as described above. For "Assay Recovery", the % number is calculated by dividing the DC009 concentration at the time point by the DC009 concentration at T=0. For "Relative purity level", the % number is calculated by (Peak area % of DC009 at Tn/Peak area % of DC009 at T0)*100%.

Example 2. Formulation Stability in Different pH Solutions

Seven formulations listed in Table 1 contained 10 mg/mL DC009 were prepared, DC009 were dissolved in each buffer and adjust to the indicated pH by NaOH and HCl.

TABLE 1

Formulation T-1~T-7

| Formulation ID | pH | Buffer |
| --- | --- | --- |
| T-1 | 4 | 5 mM sodium acetate |
| T-2 | 5 | 5 mM sodium acetate |
| T-3 | 6 | 5 mM sodium citrate |
| T-4 | 7 | 50 mM sodium phosphate |
| T-5 | 7 | DI water |
| T-6 | 7 | 0.9% NaCl |
| T-7 | 8 | 5 mM sodium phosphate |

These formulations were stored at 40° C. and 60° C. to evaluate the assay recovery and total impurity. The appearance and stability at each storage condition were recorded at Table 2 and Table 3. No precipitate was observed in any of the samples.

TABLE 2

Appearance of formulation T-1~T-7

| Formulation ID | Appearance | | |
|---|---|---|---|
| | Initial | 40° C. × 7 d | 60° C. × 7 d |
| T-1 | clear and colorless liquid | Slight yellow, clear liquid | Yellow, clear liquid |
| T-2 | clear and colorless liquid | Slight yellow, clear liquid | Yellow, clear liquid |
| T-3 | clear and colorless liquid | Slight yellow, clear liquid | Yellow, clear liquid |
| T-4 | Slight yellow, clear liquid | Light yellow, clear liquid | Yellow, clear liquid |
| T-5 | Slight yellow, clear liquid | Light yellow, clear liquid | Yellow, clear liquid |
| T-6 | Slight yellow, clear liquid | Light yellow, clear liquid | Yellow, clear liquid |
| T-7 | Light orange, clear liquid | Orange, clear liquid | Dark orange, clear liquid |

TABLE 3

Stability of formulation T-1~T-7
DC009 Assay recovery (%)

| | | | 40° C. | | 60° C. | |
|---|---|---|---|---|---|---|
| Sample | pH | T = 0 | 1 day | 4 days | 1 day | 4 days |
| T-1 | 4 | 100 | 97 | 98 | 96 | 95 |
| T-2 | 5 | 100 | 100 | 100 | 97 | 95 |
| T-3 | 6 | 100 | 99 | 98 | 97 | 91 |
| T-4 | 7 | 100 | 94 | 88 | 88 | 73 |
| T-5 | 7 | 100 | 95 | 93 | 94 | 82 |
| T-6 | 7 | 100 | 96 | 92 | 93 | 82 |
| T-7 | 8 | 100 | 87 | 63 | 73 | 45 |

In the accelerated stability study, the assay recovery of T-1 (pH 4) and T-2 (pH 5) were ≥98% at the $4^{th}$ day at 40° C., and were 95% and 60° C. The assay recovery of T-1 and T-2 at the $7^{th}$ day were 95% and 96% at 40° C., and were both 90% at 60° C. (data not shown). Whereas, the assay recovery of the formulations at pH 7-8 (T-4 to T-7) dropped below 90% after storage at for 4 days, which indicate that impurity % grew significantly. These data suggest that DC009 was stable at acidic conditions, and was very stable at pH between 4 and 5. 5 mM sodium acetate is sufficient to maintain a stable pH between pH 4 and pH 5 for a 10 mg/mL DC-009 solution.

Example 3. Formulation Stability in Different pH Solutions

In another independent experiment, 9 formulations listed in Table 4 contained 10 mg/mL DC009 were prepared, DC009 were dissolved in each buffer and adjust to the indicated pH by NaOH and HCl.

TABLE 4

Formulation P1~P6

| Sample | pH | Buffer |
|---|---|---|
| P1 | pH 7.0 | 5 mM sodium phosphate |
| P2 | pH 6.5 | 5 mM sodium phosphate |
| P3 | pH 6.0 | 5 mM sodium citrate |
| P4 | pH 5.5 | 5 mM sodium citrate |
| P5 | pH 5.0 | 5 mM sodium acetate |
| P6 | pH 4.0 | 5 mM sodium acetate |
| P7 | pH 3.5 | 5 mM sodium acetate |
| P8 | pH 2.0 | 5 mM sodium acetate |
| P9 | pH 1.0 | 5 mM sodium acetate |

These formulations were stored at 60° C. to evaluate the stability of the sample at different pH. The relative purity level of DC009 in total formulation are recorded at Table 5, the purity of DC009 is defined as 100% at T=0. Data suggest that DC009 was stable at all acidic conditions (pH<7) and maintained >95% purity level for 10 days at 60° C. After one-month storage at 60° C. (Day 38), DC009 was stable at pH 1 to pH 6 and maintained >86% purity level. The best stability was shown at pH 2.0-5.5.

TABLE 5

Stability (relative purity level %) of formulation P1-P7

| | | | 60° C. | | |
|---|---|---|---|---|---|
| Sample | pH | T = 0 | Day 5 | Day 10 | Day 38 |
| P1 | pH 7.0 | 100.00 | 95.36 | 93.18 | 70.88 |
| P2 | pH 6.5 | 100.00 | 97.94 | 97.01 | 88.28 |
| P3 | pH 6.0 | 100.00 | 99.44 | 99.17 | 92.16 |
| P4 | pH 5.5 | 100.00 | 99.67 | 99.59 | 97.74 |
| P5 | pH 5.0 | 100.00 | 99.54 | 99.28 | 97.61 |
| P6 | pH 4.0 | 100.00 | 99.53 | 99.18 | 99.23 |
| P7 | pH 3.5 | 100.00 | 99.74 | 99.73 | 99.73 |
| P8 | pH 2.0 | 100.00 | 99.98 | 99.88 | 97.78 |
| P9 | pH 1.0 | 100.00 | 99.70 | 99.39 | 86.18 |

*Relative purity level: (Peak area % of DC009 at Tn/Peak area % of DC009 at T0)*100%

Example 4A. Formulation Stability in Different Excipients

Six formulations listed in Table 6 contained 10 mg/mL DC009 and different amounts of excipients (in mg/g) were prepared, each formulation was adjusted to pH 4.5 by NaOH and HCl. These formulations were stored at 40° C. and 60° C. to evaluate the assay recovery and total impurity. Stability data are summarized in Table 7.

TABLE 6

Formulation E1~E6

| Component (mg/g) | E1 | E2 | E3 | E4 | E5 | E6 |
|---|---|---|---|---|---|---|
| DC-009 | 10 | 10 | 10 | 10 | 10 | 10 |
| Sodium acetate, anhydrous | 5 mM | 5 mM | 5 mM | 5 mM | 5 mM | 5 mM |
| EDTA2Na2H$_2$O | 0.055 | 0.055 | 0.055 | 0.055 | 0.055 | 0.055 |
| Glycine | 22 | | | | | |
| Lactose | | 90 | | | | |
| Mannitol | | | 50 | | | |
| Trehalose dihydrate | | | | 90 | | |
| Sucrose | | | | | 90 | |

TABLE 7

Stability of formulation E1~E5
DC009 Assay recovery (%)

| Sample | Main Excipient (ME) | 40° C. T = 0 | 40° C. 2 Weeks | 40° C. 4 Weeks | 60° C. 1 Week | 60° C. 2 Weeks | DC009/ME weight ratio |
|---|---|---|---|---|---|---|---|
| E1 | Glycine | 100 | 93 | 82 | 65 | 51 | 1:2.2 |
| E2 | Lactose | 100 | 99 | 100 | 95 | 90 | 1:9 |
| E3 | Mannitol | 100 | 100 | 101 | 96 | 90 | 1:5 |
| E4 | Trehalose | 100 | 100 | 102 | 96 | 92 | 1:9 |
| E5 | Sucrose | 100 | 99 | 100 | 96 | 91 | 1:9 |
| E6 | — | 100 | 98 | 97 | 92 | 80 | — |

In the accelerated stability study, the assay recovery of E2-E5 were ≥90% at 2 weeks at 60° C. (Table 7). E1 glycine excipient significantly reduced the stability comparing with control E6, whereas mannitol, trehalose, sucrose, and lactose improved the stability comparing with control E6.

Example 4B. Formulation Stability in Different Excipients

In a separate experiment, different excipients list on Table 8 were tested for the effect on stabilizing DC009. For formulation S1-S10, 10 mg/mL DC009 were prepared in 5 mM Sodium acetate buffer, the concentration of each excipient is 3.8% and the pH of the formulations were adjusted to pH 4.5. These formulations are store at 60° C. for two weeks. The relative purity level of DC009 in total formulation were recorded at Table 8, the purity of DC009 were defined as 100% at T=0. The purity level of S1 and S3 were >80% at 2 weeks at 60° C. The results show that mannitol and sorbitol provided better stability than other excipients.

TABLE 8

Stability (relative level in %) of formulation S1~S10

| Sample | Excipient | Day 0 | Day 6 | Day 10 | Day 14 |
|---|---|---|---|---|---|
| S1 | Mannitol | 100.00 | 90.33 | 89.01 | 88.92 |
| S2 | Maltose | 100.00 | 84.43 | 81.58 | 69.91 |
| S3 | Sorbitol | 100.00 | 88.71 | 85.57 | 81.47 |
| S4 | Arginine | 100.00 | 81.96 | 68.01 | 56.00 |
| S5 | Glucose | 100.00 | 82.91 | 61.12 | 46.77 |
| S6 | Raffinose | 100.00 | 87.72 | 67.89 | 48.89 |
| S7 | Ethylene glycol | 100.00 | 72.68 | 59.53 | 50.83 |
| S8 | Dextose | 100.00 | 83.16 | 62.49 | 45.60 |
| S9 | Maltitol | 100.00 | 88.77 | 83.75 | 74.74 |
| S10 | Histidine | 100.00 | 88.76 | 78.86 | 69.85 |

Example 5. Stability in Formulations Containing Mannitol

Four formulations listed in Table 9 containing 10 mg/mL DC009 were prepared, each formulation was adjusted to pH 4.5 by NaOH and HCl. M1-M3 contained 50 mg/g D-mannitol, and M4 did not contain D-mannitol. These formulations were stored at 40° C. and 60° C. to evaluate the assay recovery. The stability results at each storage condition are recorded at Table 10.

TABLE 9

Formulation M1~M4

| Component (mg) | M1 | M2 | M3 | M4 |
|---|---|---|---|---|
| DC-009 | 10 | 10 | 10 | 10 |
| Sodium acetate, anhydrous | | 5 mM | 5 mM | 5 mM |
| EDTA2Na2H₂O | | | 0.055 | 0.055 |
| D-mannitol | 50 | 50 | 50 | |

TABLE 10

Stability of formulation M1~M4
DC009 Assay recovery (%)

| Sample | T = 0 | 40° C. 2 Weeks | 40° C. 4 Weeks | 60° C. 1 Week | 60° C. 2 Weeks |
|---|---|---|---|---|---|
| M1 | 100 | 98 | 99 | 95 | 94 |
| M2 | 100 | 98 | 99 | 95 | 92 |
| M3 | 100 | 100 | 101 | 96 | 90 |
| M4 | 100 | 98 | 97 | 92 | 80 |

In the accelerated stability study, the assay recovery of M1-M3 were ≥90 at 2 weeks at Data suggest that adding mannitol improved the formulation stability comparing with the M4 formulation without mannitol.

Example 6. Formulation Stability Study Lipolyzed Formulation

Two formulations listed in Table 11 were prepared. Each formulation was lyophilized in a lyophilizer and was stored at 25° C. and 40° C. to evaluate the assay recovery. The stability results at each storage condition are summarized in Table 12.

TABLE 11

Lyophilized formulation

| Component | F-1 | F-1H |
|---|---|---|
| DC009 | 1 | 2 |
| Mannitol | 3.8 | 2.6 |
| DI Water | QS to 100 | QS to 100 |
| 1N NaOH/HCl to pH 4.5 | + | + |
| DC009/mannitol ratio | 1:3.8 | 1:1.3 |

TABLE 12

Stability of lyophilized formulations
DC009 Assay recovery (%)

| | T = 0 | 1 month | | 2 months | | 3 months | |
|---|---|---|---|---|---|---|---|
| Sample | 25° C. | 25° C. | 40° C. | 25° C. | 40° C. | 25° C. | 40° C. |
| F1 | 100 | 103 | 101 | 101 | 102 | 102 | 102 |
| F1-H | 100 | 99 | 98 | 100 | 99 | 99 | 95 |

Two stable solution intravenous lyophilized formulations (F-1 and F-1H) were developed for DC009 at 10 mg/mL and 20 mg/mL, respectively. Based on the stability tests conducted, F-1 and F-1H were physically and chemically stable at 25° C. and 40° C. for 3 months. The lyophilized formulations can be reconstituted with normal saline before intravenous injection.

The invention, and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the scope of the present invention as set forth in the claims. To particularly point out and distinctly claim the subject matter regarded as invention, the following claims conclude the specification.

What is claimed is:

1. A pharmaceutical composition comprising a compound with the following formula or a pharmaceutically acceptable salt thereof:

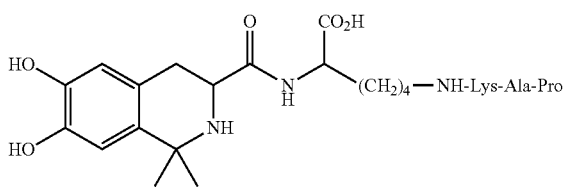

and a pharmaceutically acceptable carrier, wherein the composition has a pH<6.5.

2. The pharmaceutical composition according to claim 1, wherein the composition has a pH of about pH 1-pH 6.

3. The pharmaceutical composition according to claim 1, wherein the composition has a pH of about pH 2-pH 6.

4. The pharmaceutical composition according to claim 1, wherein the composition has a pH of about pH 2-pH 5.5.

5. The pharmaceutical composition according to claim 1, wherein the composition has a pH of about pH 3.5-pH 5.5.

6. The pharmaceutical composition according to claim 5, wherein the composition has a pH of about pH 4.5.

7. The pharmaceutical composition according to claim 1, wherein the pharmaceutically acceptable salt is hydrochloride salt.

8. A pharmaceutical composition comprising a compound with the following formula or a pharmaceutically acceptable salt thereof:

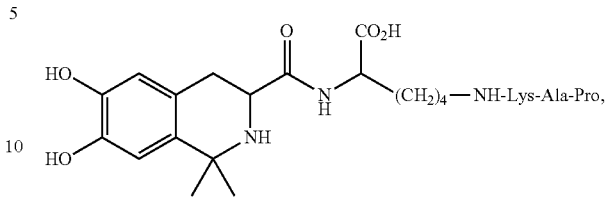

and a pharmaceutically acceptable excipient, wherein the composition has a pH of pH<6.5, wherein the pharmaceutically acceptable excipient is mannitol, sorbitol, sucrose, lactose, or trehalose.

9. The pharmaceutical composition according to claim 8, wherein the pharmaceutically acceptable excipient is mannitol.

10. The pharmaceutical composition according to claim 8, wherein the weight ratio of the compound versus the pharmaceutically acceptable excipient is about 1:1 to 1:9.

11. The pharmaceutical composition according to claim 10, wherein the weight ratio of the compound versus the pharmaceutically acceptable excipient is about 1:1 to 1:5.

12. The pharmaceutical composition according to claim 11, wherein the pharmaceutically acceptable excipient is mannitol.

13. The pharmaceutical composition according to claim 12, wherein the composition has a pH of about pH 3.5-pH 5.5.

14. The pharmaceutical composition according to claim 13, wherein the composition is a lyophilized formulation.

15. The pharmaceutical composition according to claim 8, wherein the pharmaceutically acceptable salt is hydrochloride salt.

* * * * *